United States Patent [19]

Meilland, deceased

[11] Patent Number: Plant 6,895

[45] Date of Patent: Jul. 4, 1989

[54] ROSE PLANT—MEIVILDO VARIETY

[75] Inventor: Marie-Louise Meilland, deceased, late of Antibes, France, by Jean-Pierre La Naour, executor

[73] Assignee: The Conard-Pyle Company, West Grove, Pa.

[21] Appl. No.: 187,327

[22] Filed: Apr. 28, 1988

[51] Int. Cl.[4] ..... A01H 5/00

[52] U.S. Cl. ..... Plt./18

[58] Field of Search ..... Plt./18

*Primary Examiner*—James R. Feyrer

*Attorney, Agent, or Firm*—Burns, Doane, Swecker & Mathis

[57] ABSTRACT

A new and distinct variety of Hybrid Tea rose plant is provided which forms abundantly and continuously attractive very double neyron pink blossoms which possess a long vase life. The blossoms exhibit a pleasing fragrance and initially possess a globular configuration. The petals are serrated and drop off cleanly. The plant is not particularly affected by cryptogamic diseases.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was formed by the pollination of an unnamed seedling which was the product of the pollination of the Meifiga variety (non-patented) by the Mme A. Meilland variety (U.S. Plant Pat. No. 591) by an unnamed seedling resulting from the pollination of the Chrysler Imperial variety (U.S. Plant Pat. No. 1,167) by the Charles Mallerin variety (non-patented). The Mme. A. Meilland variety commonly is called the PEACE variety in the United States. The male parent (i.e., the pollen parent) was the Meidanu variety (non-patented). The parentage of the new variety can be summarized as follows:

[(Meifiga × Mme. A. Meilland) × (Chrysler Imperial × Charles Maller in)] × [Meidanu].

The seeds resulting from the above pollination were sown and 97 plantlets were obtained which were physically and biologically different from each other. Selective study resulted in the identification of a single plant of the new variety.

It was found that the new variety of Hybrid Tea rose plant of the present invention possesses the following combination of characteristics:

(a) exhibits a semi-erect growth habit,
(b) forms in abundance on a continuous basis long lasting very double neyron pink blossoms having serrated petals which exhibit a pleasing fragrance and initially are globular shaped,
(c) forms strong vigorous vegetation, and
(d) is not particularly affected by cryptogamic diseases.

The new variety well meets the needs of the horticultural industry. It is particularly well suited for growing as ornamentation in parks and gardens.

The new variety has been found to undergo asexual propagation by a number of routes, including budding, grafting, cuttage, etc. The characteristics of the new variety have been found to be strictly transmissible by such asexual propagation from one generation to another.

The new variety has been named the Meivildo variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were one year of age and were observed during July while grafted on *Rosa froebelii* and growing in the open air at Cannet-des-Maures, Var, France.

DETAILED DESCRIPTION

Figures 1, 2, 3, 4, 5, 6, 7, 8, 9, 10, 11, 12, 13, 14, 15, 16:
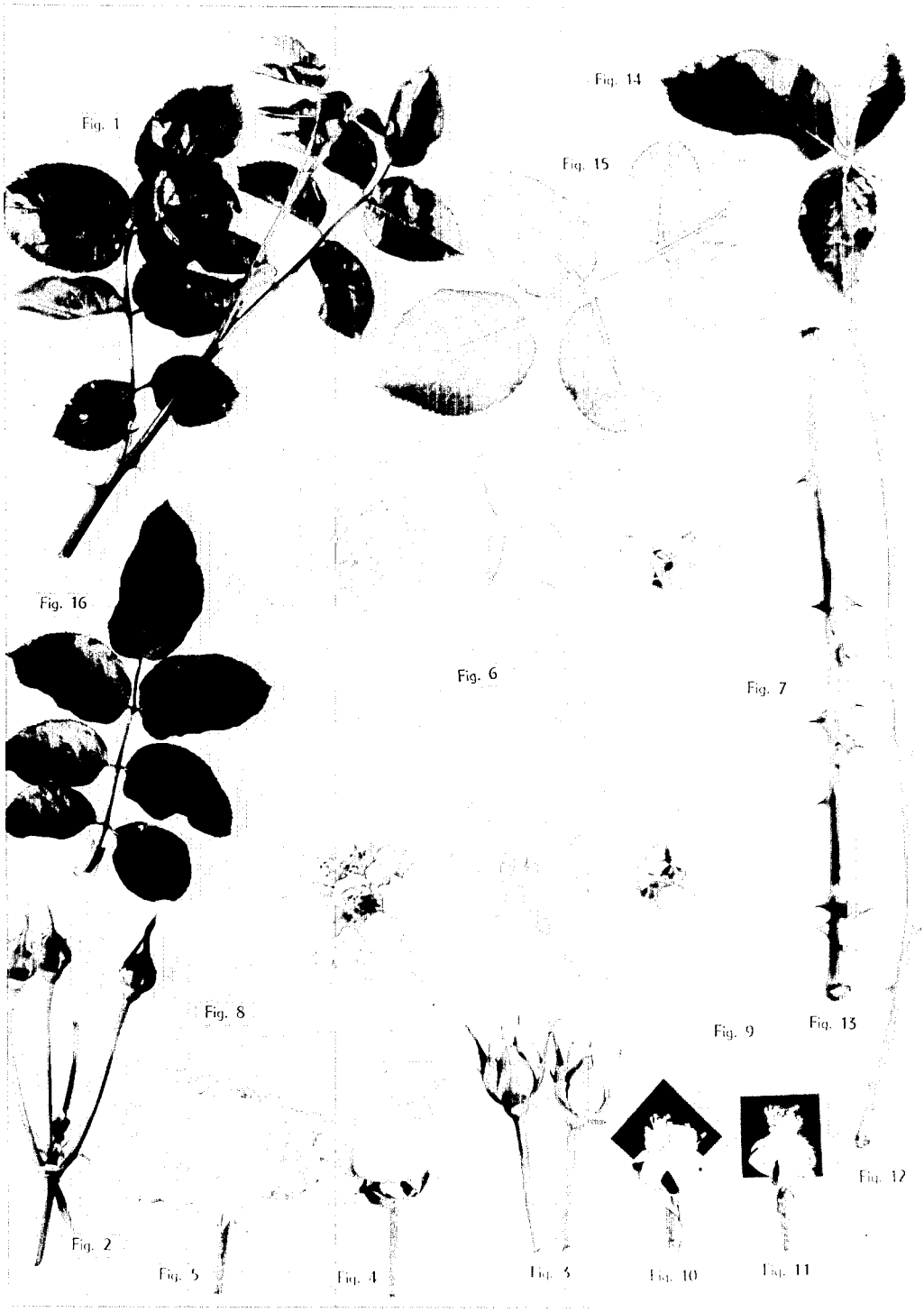
FIG. 1 illustrates a specimen of a young shoot.
FIG. 2 illustrates a specimen of three floral buds before the opening of the sepals.
FIG. 3 illustrates specimens of two floral buds at the opening of the sepals.
FIG. 4 illustrates a specimen of a floral bud at the opening of the petals.
FIG. 5 illustrates a specimen of a flower in the course of opening.
FIG. 6 illustrates a specimen of a fully open flower — plan view — obverse.
FIG. 7 illustrates a specimen of a fully open flower — plan view — reverse.
FIG. 8 illustrates a specimen of a fully open flower immediately prior to petal drop — plan view — obverse.
FIG. 9 illustrates a specimen of a fully open flower immediately prior to petal drop — plan view — reverse.
FIG. 10 illustrates a specimen of a floral receptacle showing the arrangement of the stamens.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates a specimen of a leaf with three leaflets — plan view — upper surface.
FIG. 15 illustrates a specimen of a leaf with five leaflets — plan view — under surface.
FIG. 16 illustrates a specimen of a leaf with seven leaflets — plan view — upper surface.

The chart used in the identification of the colors is that of The Royal Horticultural Society (R.H.S. Colour Chart). The description is based on one year old plants made during July while grafted on *Rosa froebelii* understock and growing in the open air at Cannet-des-Maures, Var, France. The coloration in common terms precedes reference to the chart.

Class: Hybrid Tea.

Plant:

*Height.*—85 cm. on average.

*Habit.*—Semi-erect.

Branches:

*Color.*—Young stems: light green, Yellow-Green Group 146C, more or less shaded with a reddish tint. Adult wood: medium green, Yellow-Green Group 146B.

Leaves:

*Stipules.*—Adnate, pectinate, very wide and linear.

*Petioles.*—Upper surface: grooved, reddish brown on young leaves and medium green on adult foliage. Under surface; light green with glandular edges, bear some hooked thorns.

*Leaflets.*—Number: 3, 5 and 7 (most often). Shape: elliptic with a rounded base. Serration: simple and regular. Texture: leathery. General appearance: ample and dense foliage with a semi-glossy aspect. Color (young foliage): upper surface: reddish brown. under surface: reddish brown. Color (adult foliage): upper surface: dark green, Yellow-Green Group 147A. under surface: light green, Yellow-Green Group 147B.

Inflorescence:

*Number of flowers.*—Generally one per stem.

*Peduncle.*—Straight, rigid, medium green in coloration, and often shaded with reddish brown. The length is approximately 4.0 cm. on average.

*Sepals.*—Upper surface: tomentose, greenish in coloration. Under surface: light green and more or less shaded with a reddish tint, the edges are more or less glandular, and the outside petals have more or less appendiculated edges.

*Buds.*—Shape: globular. Length: approximately 4.0 cm. on average. Size: fairly large. Color upon opening: upper surface: neyron pink, Red Group 55A. under surface: spinel pink, Red Group 54B.

*Flower.*—Shape: ancient, very special, initially globular changing to the configuration of a cup. Diameter: approximately 13 cm. on average. Color (when opening begins): upper surface: neyron pink, Red Group 55A. under surface: spinel pink, Red Group 54B. Color (when blooming): upper surface: pale neyron pink, Red Group 55A. under surface: light spinel pink, Red Group 54B. Color (at end of opening): upper surface: pale neyron pink, Red Group 55B. under surface: spinel pink, Red Group 54B. Fragrance: strong. Lasting quality: long. Petal number: approximately 80 on average. Petal form: rounded with serrated edges. Texture: quite firm. Petal drop: good. Stamen number: approximately 93 on average. Anthers: normal, light yellow in coloration. Filaments: pink tinted with a yellow base, of irregular heights. Pistils: approximately 73 on average. Stigmas: normal, straw colored. Styles: straw yellow in coloration, very tomentose, of irregular heights. Receptacle: medium green, in longitudinal section are wide and in the shape of a jug.

Development:

*Vegetation.*—Very vigorous.

*Blooming.*—Abundant and continuous.

*Aptitude to bear fruit.*—None.

*Resistance to frost.*—Good.

*Resistance to diseases.*—Very good.

It is claimed:

1. A new and distinct variety of Hybrid Tea rose plant characterized by the following combination of characteristics:

(a) exhibits a semi-erect growth habit, (b) forms in abundance on a continuous basis long lasting very double neyron pink blossoms having serrated petals which exhibit a pleasing fragrance and initially are globular shaped, (c) forms strong vigorous vegetation, and (d) is not particularly affected by cryptogamic diseases, substantially as herein shown and described, together with the parts thereof.

* * * * *